United States Patent [19]

Imamura et al.

[11] Patent Number: 4,804,533
[45] Date of Patent: Feb. 14, 1989

[54] METAL SALTS OF MONOALKYL PHOSPHATES, PREPARATION THEREOF, AND COSMETIC COMPOSITIONS COMPRISING SAME

[75] Inventors: Takashi Imamura; Norio Nishigawa, both of Wakayama; Tomihiro Kurosaki, Sennan; Junichi Fukasawa, Chiba; Haruya Kato, Funabashi, all of Japan

[73] Assignee: Kao Corporation, Tokyo, Japan

[21] Appl. No.: 44,198

[22] Filed: Apr. 30, 1987

Related U.S. Application Data

[62] Division of Ser. No. 736,845, May 22, 1985, abandoned.

[30] Foreign Application Priority Data

May 25, 1984 [JP] Japan .................. 59-106136
May 25, 1984 [JP] Japan .................. 59-106137
Apr. 5, 1985 [JP] Japan .................. 60-72317

[51] Int. Cl.$^4$ ............................................. A61K 7/035
[52] U.S. Cl. .......................................... 424/69; 424/63
[58] Field of Search ......................... 424/401, 63, 69

[56] References Cited

U.S. PATENT DOCUMENTS 3,491,133 1/1970 Revukas .................. 556/24
3,632,744 1/1972 Paulsen .................. 424/69
4,163,018 7/1979 Tada et al. .............. 558/133 X

FOREIGN PATENT DOCUMENTS 0125852 11/1984 European Pat. Off. .
154150 9/1985 European Pat. Off. .......... 424/69
1135262 12/1968 United Kingdom .
2160527 12/1985 United Kingdom .............. 424/69

OTHER PUBLICATIONS

Chemical Abstracts, vol. 102, No. 8, Feb. 25, 1985, p. 34, No. 63048s.

*Primary Examiner*—George F. Lesmes
*Assistant Examiner*—Susan S. Rucker
*Attorney, Agent, or Firm*—Oblon, Fisher, Spivak, McClelland & Maier

[57] ABSTRACT

Metal salts of monoalkyl phosphates of the following formula

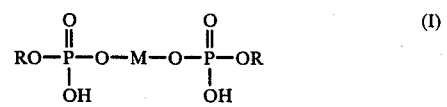

(I)

in which each R represents a saturated or unsaturated, linear or branched hydrocarbon group having from 8 to 32 carbon atoms, and M represents an alkaline earth metal or divalent transition metal.

The metal salts are particularly suitable as cosmetic powders, fillers for resins, and lubricants, parting agents and pigment dispersants for polymeric compounds. When used as cosmetic powders, the metal salts improve spreadability, moistness, smoothness, adherence, transparency and covering power of cosmetics.

Preparation process of the metal salts is also disclosed.

7 Claims, 4 Drawing Sheets

METAL SALTS OF MONOALKYL PHOSPHATES, PREPARATION THEREOF, AND COSMETIC COMPOSITIONS COMPRISING SAME

This is a division of application Ser. No. 736,845, filed May 22, 1985 now abandoned.

BACKGROUND OF THE INVENTION (i) Field of the Invention

This invention relates to metal salts of monoalkyl phosphates, preparation thereof, and cosmetic compositions comprising same and cosmetic powders.

(ii) Description of the Prior Art:

A variety of cosmetics comprising powders are known including makeup cosmetics such as foundations, face powders, powder eye shadows, powder eyebrows and the like, and body cosmetics such as body powders, baby powders and the like. The powders used in these cosmetics may be inorganic body extender pigments such as talc, kaolin, sericite, mica and the like; inorganic colorants such as titanium dioxide, zinc oxide, ultramarine blue, chromium oxide, iron oxides and the like; organic colorants such as organic synthetic dyes, lakes and the like; composite pigments such as titanium-dioxide coated mica, iron oxide-coated mica and the like; and treated powders obtained by coating the above-indicated powders with known coating materials such as silicone oils, higher fatty acids, higher alcohols, esters, waxes and the like. The properties of these cosmetics depend largely on the properties of the powders. However, these known powders are not satisfactory in imparting all properties necessary for good cosmetics, e.g. lubricity, flow-out, moistness, a suitable degree of adherence, and the like. In order to impart such properties, it is now the usual practice to add metallic soap to powder-containing cosmetics. Metallic soap is believed to impart moistness, lubricity, flow-out, adherence, and covering power to cosmetics. However, metallic soap used as a starting material for cosmetics does not impart satisfactory properties to final cosmetic articles. In conventional powder-pressed cosmetics, oils such as hydrocarbons, esters, waxes, silicones and the like are added for the purpose of improving press moldability. These oils tend to give adverse influences on the lubricity and flow-out of metallic soap. In final products, the properties of metallic soap are rarely utilized efficiently.

Other materials for cosmetics which are able to impart lubricity and flow-out include spherical polymer powders such as nylon powders, styrene copolymers, and the like. These materials are dry to the touch and poor in adherence, so that they cannot impart suppleness and moistness to cosmetics. Thus, such cosmetics becomes poor in adherence to the skin with a lowering of press moldability.

SUMMARY OF THE INVENTION

Under these circumstances in the art, the present inventors made intensive studies to develop cosmetic compositions which were free of the disadvantages of the prior art cosmetic compositions and which had good feel in practical applications. As a result, it was found that a specific type of metal salt of alkyl phosphate had good characteristic properties as a base material for cosmetic compositions. More particularly, when added to cosmetic compositions, the metal salt exhibited good lubricity and flow-out. When such cosmetic composition was spread on the skin, gradual development of softness, an appropriate degree of adherence and covering power was experienced. Even though the metal salt was added to powder cosmetic compositions to be press molded in which oils were added in order to improve the binding force, the resulting cosmetic involved little lowering of the feel to the touch. The present invention is accomplished based on the above findings.

It is therefore an object of the present invention to provide novel metal salts of monoalkyl phosphates of the following formula in which each R represents a saturated or unsaturated, linear or branched hydrocarbon group having from 8 to 32 carbon atoms, and M represents an alkaline earth metal or divalent transition metal. These metal salts are particularly suitable as cosmetic powders, fillers for resins, and lubricants, parting agents and pigment dispersants for polymeric compounds.

It is another object of the invention to provide a novel process for preparing the metal salts of monoalkyl phosphates of the above formula (I).

It is a further object of the invention to provide cosmetic compositions which comprise the metal salts (I) of monoalkyl phosphates and cosmetic powders.

DETAILED DESCRIPTION OF THE INVENTION AND PREFERRED EMBODIMENTS

The metal salts (I) of monoalkyl phosphates of the present invention are prepared by reaction between monoalkyl phosphates of the formula (II) and metal salts of the formula (III) according to the following reaction formula in which X represents hydrogen or an alkali metal, Y represents an inorganic anion, an organic carboxylic acid anion or oxygen, m and n are, respectively, integers corresponding to the valences of Y and M, and R and M have, respectively, the same meanings as defined before.

Metal salts of phosphoric monoesters have been conventionally prepared according to the following processes.

(1) Metal salts of phosphoric monoesters are prepared by thermal reaction between phosphoric monoesters and metal acetates other than alkali metal acetates at temperatures or over at which acetic acid is capable of being evaporated sufficiently (Japanese Patent Publication No. 42-12646).

(2) Metal salts of phosphoric monoesters are prepared by reaction between dialkali salts of phosphoric monoesters, which have been obtained by neutralizing phosphoric monoesters with alkali hydroxide to an extent of two equivalent points of the phosphoric monoesters, and inorganic metal salts (Japanese Laid-open Patent Application No. 53-84919).

(3) Metal salts derivatives of phosphoric monoesters are prepared by reaction between dialkali metal salts of phosphoric monoesters and inorganic metal salts in the presence of alkali metal hydroxide (Japanese Laid-open Patent Application No. 54-141727).

However, metal salts of phosphoric monoesters obtained by the above processes are different from the compounds of the formula (I) according to the invention. As will be seen from the specifications of the above references, the processes (1) and (2) provide compounds of the formula (IV) and the process (3) provides compounds of the formula (V) indicated below in which each R and M have the same meanings as defined before, respectively.

We have found that when monoalkyl phosphates or monoalkali metal salts thereof are reacted with divalent metal salts, 2 moles of the monoalkyl phosphate are reacted with one mole of the divalent metal salt, thereby producing metal salts of monoalkyl phosphates of the present invention.

The hydrocarbon groups represented by R in the formulae (I) and (II) include, for example, octyl, nonyl, decyl, dodecyl, undecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, octenyl, nonenyl, decenyl, dodecenyl, undecenyl, tridecenyl, tetradecenyl, pentadecenyl, hexadecenyl, heptadecenyl, octadecenyl, nonadecenyl, eicocenyl, heneicocenyl, dococenyl, tricocenyl, tetracocenyl, pentacocenyl, hexacocenyl, heptacocenyl, octacocenyl, nonacocenyl, triacontenyl, hentriacontenyl, dotriacontenyl, octadienyl, nonadienyl, decadienyl, dodecadienyl, undecadienyl, tridecadienyl, tetradecadienyl, pentadecadienyl, hexadecadienyl, heptadecadienyl, octadecadienyl, nonadecadienyl, eicosadienyl, heneicosadienyl, docasadienyl, tricosadienyl, tetracosadienyl, pentacosadienyl, hexacosadienyl, heptacosadienyl, octacosadienyl, nonacosadienyl, triacontadienyl, hentriacontadienyl, dotriacontadienyl, 2-hexyldecyl, 2-octylundecyl, 2-decyltetradecyl, 2-undecylhexadecyl, 2-tetradecyloctadecyl, and the like.

The monoalkyl phosphates used as one of starting materials may inevitably comprise, in view of the manner of preparation, dialkyl phosphates, phosphoric acid, and unreacted alcohol. The purity of monoalkyl phosphates generally gives a great influence on the crystal form of an intended metal salt of monoalkyl phosphate.

If the metal salt of monoalkyl phosphate is obtained as a crystal form of a needle, plate or flake, it shows satisfactory characteristic properties as a smooth powder. Even though the above impurities are contained in a total amount of about 50%, formation of an intended metal salt is not impeded, but the characteristic properties may lower considerably without giving such a specific crystal form as mentioned above, which depends on the type of metal, M. In this sense, the purity of the monoalkyl phosphate is generally in the range of 80 wt% (hereinafter referred to simply as %) or higher, preferably 95% or higher. The dialkyl phosphate should preferably not larger than 20 mole%, most preferably not larger than 5 mole%, of the monoalkyl phosphate. Similarly, phosphoric acid is preferably not larger than 5%, most preferably not larger than 1% and the unreacted alcohol is preferably not larger than 3%, most preferably not larger than 1%, each based on the monoalkyl phosphate.

The monoalkyl phosphate used as the starting material for the reaction of the present invention may be a free acid where X in the afore-defined formula is hydrogen, or a monoalkali metal salt where X is an alkali metal, or may be a mixture of these free acid and metal salt in arbitrary mixing ratios. However, if dialkali metal salts are present, the compound of the formula (IV) is secondarily produced according to the prior art process, thus impeding formation of the crystal form inherent to the compound of the formula (I). Accordingly, smaller contents of dialkali metal salts are preferred and the contents of dialkali metal salts should not be larger than 25 mole%, preferably not larger than 5 mole%, based on the monoalkali metal salt of monoalkyl phosphate.

The monoalkali metal salt of monoalkyl phosphate is prepared by a method of neutralizing a monoalkyl phosphate with an alkali metal hydroxide to an extent of the first equivalence point, or by a method in which a dialkali metal salt is cation-exchanged using ion exchange resins or acids. In the former method, a monoalkyl phosphate is dissolved under heating conditions in an inert solvent such as acetone, ethanol, methanol or water, and adding an aqueous alkali metal hydroxide solution at a temperature of from 20° to 80° C., preferably from 40° to 60° C. for neutralization to such an extent of the first equivalence point.

The divalent metals represented by M in the metal salt of the formula (III) include, for example, alkali earth metals such as Mg, Ca, Ba and the like, and divalent transition metals such as Zn, Cu, Ni, Co, Fe, Mn, Cd, Pb, Cr, Ti and the like. Of these, Ca, Mg, Ba, Zn, Fe and Ni are preferred. Specific examples of Y in the formula include inorganic anions such as halogens, $SO_4$, $NO_3$, $CO_3$, $PO_4$, OH and the like; anions of organic carboxylic acids such as acetic acid, propionic acid, citric acid and the like; and oxygen. Of these halogens, $SO_4$, $PO_4$, $NO_3$ and $CO_3$ are preferred. The metal salts of the formula (III) are preferably soluble in water and preferable examples include $CaCl_2$, $MgCl_2$, $FeCl_2$. $ZnCl_2$, $ZnSO_4$, $MgSO_4$, $FeSO_4$, and $Ni(NO_3)_2$.

Monoalkyl phosphate (II) and metal salt (III) are reacted in an inert solvent at a temperature of from 10° to 80° C., preferably 40° to 70° C. The amount of metal salt (III) is not less than 0.5 moles, preferably from 0.5 to 0.55 moles, per mole of monoalkyl phosphate. The inert solvents used for the reaction include organic solvents such as acetone, ethanol and the like when monoalkyl phosphates (free acid) are used. On the other hand, when monoalkali metal salts of monoalkyl phosphates are used, water is preferably used. In this connection, if the reaction is carried out using an economical concentration of a monoalkali metal salt (II') of monoalkyl phosphate, i.e. not less than 20%, it is preferred to use a mixed solvent of water and a solvent miscible with water. This is because when the reaction is effected using water as solvent and a concentration of a monoalkali metal salt of monoalkyl phosphate not less than 20%, crystals of the alkali metal salt coagulate to a substantial extent, so that the resulting powder is not so good with regard to spreadability, smoothness and the like. On the other hand, when a mixed solvent of water and an organic solvent miscible with water in a certain mixing ratio is used, there is prepared monoalkyl phosphate metal salt (I) having good properties in high concentration and economically.

The mixed solvent should preferably contain water and organic miscible solvents in a mixing ratio of 99/1 to 20/80 on the weight basis.

Examples of the miscible solvent include acetone, methanol, ethanol, iso-propyl alcohol, n-propyl alcohol, n-butyl alcohol, sec-butyl alcohol, t-butyl alcohol, ethylene glycol, diethylene glycol, acetonitrile, tetrahydrofuran, dioxane, dimethylformamide, dimethyl sulfoxide, and the like. These solvents may be used singly or in combination. Of these, acetone, methanol, ethanol, iso-propyl alcohol, and n-propyl alcohol are preferred.

If water alone or a mixed solvent having a content of a water-miscible solvent of less than 1% is used, a disadvantage is involved in that when the concentration of the monoalkali metal salt of monoalkyl phosphate in the reaction solvent exceeds 20%, crystals tend to coagulate. As a result, the resulting metal salt of monoalkyl phosphate (I) does not show a crystal form of needle, plate or flake, causing characteristic properties such as spreadability, smoothness and the like, to become poor. Even when the concentration of the monoalkali metal salt of monoalkyl phosphate (II') in the reaction solvent is below 20%, crystals will coagulate as the concentration increases. However, when the content of a miscible solvent in the reaction solvent is over 1%, the resulting metal salt of monoalkyl phosphate (I) is obtained in the form of needle, plate or flake, even if the concentration of the monoalkali salt (II') exceeds 20%. On the other hand, when the content of a miscible solvent in the reaction solvent exceeds 80%, the monoalkali metal salt (II') unfavorably precipitates in large amounts.

When a mixed solvent is used as the reaction solvent, the concentration of the monoalkali metal salt of monoalkyl phosphate (II') is generally not larger than 90%, preferably not larger than 50%. Higher concentrations result in a higher efficiency, but the viscosity becomes so high that it is difficult to handle.

The mixing of water with miscible solvents may be carried out by several methods including a method in which a corresponding monoalkyl phosphate is neutralized with an aqueous alkali metal hydroxide solution in a solvent miscible with water, and the resulting solution is used, as it is, for reaction with a metal salt of the formula (III); a method in which a monoalkyl phosphate is neutralized with an alkali metal hydroxide in a mixed solvent of water and a miscible solvent, and the resulting solution is used, as it is, for reaction with a metal salt of the formula (III); and a method of separating an alkali metal salt of monoalkyl phosphate as solid and adding the solid to a mixed solvent of water and a miscible solvent. As a matter of course, non-aqueous solvents which do not affect the reaction may be added to the mixed solvent of water and miscible solvents.

The metal salt (III) is used for reaction as an aqueous solution, or as solid. When the metal salt is added in the form of an aqueous solution, the metal salt (III) should be preferably used in high concentrations from the standpoint of production efficiency.

The reaction solution obtained is cooled to cause crystals to be separated, followed by filtering, washing with water and drying to obtain crystals of a metal salt of monoalkyl phosphate.

The thus obtained metal salt of the present invention has the crystal form of needle, plate or flake and good characteristic properties as is different from the known metal salt of phosphoric monoester (IV) or (V). Especially, the metal salt of the invention is useful and effective as a cosmetic powder. For instance, the metal salt is favorably added to pressed face powders, powder foundations, powder eye shadows and the like.

The other essential ingredient used in cosmetic compositions of the invention is a cosmetic powder. The cosmetic powder may include any known powders used for cosmetic purposes. Examples of the powder include inorganic body pigments such as talc, sericite, mica, kaolin and the like, inorganic colorants such as titanium dioxide, zinc oxide, ultramarine blue, chromium oxide, iron oxides and the like; organic colorants such as organic tar dyes, lakes and the like, composite pigments such as titanium dioxide-coated micro, iron oxide-coated mica and the like, and these powders coated with known coating materials such as silicone oils, higher fatty acids, higher alcohols, esters, waxes and the like. These powders may be used singly or in combination. For the purpose of makeup cosmetics and body cosmetics, inorganic powders such as talc, sericite, mica, kaolin, titanium dioxide, titanium dioxide-coated mica, iron oxide-coated mica and the like, are preferred.

For the preparation of the cosmetic composition of the invention, there may be used, aside from the essential ingredients such as metal salts of alkyl phosphates and cosmetic powders, suitable amounts of arbitrary ingredients ordinarily used for these purposes, e.g. various oils, surface active agents, humectants, preservatives, antioxidants, perfumes and the like. Examples of the oil include liquid paraffin, vaseline, paraffin wax, squalane, sericin wax, bees wax, carnauba wax, candelilla wax, hardened castor oil, olive oil, lanolin, lanolin alcohols, lanolin fatty acids, higher alcohols, fatty acids, synthetic ester oils of higher alcohols and fatty acids, silicone oils and the like. Examples of the surface active agent include polyoxyethylene alkyl ethers, polyoxyethylene fatty acid esters, polyoxyethylene sorbitan fatty acid esters, sorbitan fatty acid esters, glycerine fatty acid esters, polyoxyethylene hardened castor oil, polyoxyethylene sorbitol fatty acid esters and the like. Examples of the humectant include sorbitol, glycerine, propylene glycol, 1,3-butylene glycol, lactic acid, sodium lacate, polyethylene glycol and the like. Examples of the preservative include alkyl paraoxybenzoates, sodium benzoate, potassium sorbate, phenoxy ethanol and the like. Examples of the antioxidant include tochopherol, sesamol, sesamolin, lecithin and the like.

The amount of the metal salt of alkyl phosphate in the cosmetic composition of the invention is generally in the range of from 0.1 to 99%. With powder pressed cosmetics, the amount is preferably in the range of from 0.1 to 30%. Less amounts do not show an appreciable effect of the metal salt, whereas larger amounts are unfavorable because when the surface of a press molded cosmetic is rubbed with a cosmetic puff several times, it may become glossy. The cosmetic powders are preferably used in amount of from 70 to 99.9% of the total composition.

The cosmetic compositions of the invention are prepared by mixing the essential ingredients of a metal salt of an alkyl phosphate and a cosmetic powder, and arbitrary ingredients such as in a Henschel mixer, Nauta mixer (screw mixer), ribbon blender, or mortar, and molding the mixture in a desired form, if necessary. The cosmetic compositions of the invention may be prepared into makeup cosmetics such as foundations, rouges, eye shadows, eye brows and the like; and body cosmetics such as body powders, baby powders and the like.

The cosmetic compositions of the invention exhibit much better smoothness and spreadability than conventional ones. In addition, the cosmetic compositions of the invention have such characteristic properties that during spreading on the skin, the moistness, a suitable degree of adherence, and covering power develops.

The present invention is described by way of examples and comparative examples.

EXAMPLE 1

Ca Salt of Monolauryl Phosphate

Four hundred grams of ethanol and 100 g of monolauryl phosphate (molecular weight of 266) were placed in a reactor and mixed for dissolution at 60° C. Into the solution was gradually dropped an aqueous solution of 27.6 g of $CaCl_2.2H_2O$ in 160 g of water, followed by mixing at 60° C. for 1 hour to complete the reaction. Subsequently, the reaction solution was cooled down to 30° C. and filtered. The resulting filter cake was washed twice with each 400 g of ethanol, once with 500 g of water, and once with 400 g of acetone, followed by drying to obtain 96 g of the intended compound in the form of white powder. Observation through a scanning electron microscope revealed that the compound was in the form of needle crystals having a length below 30 μm.

| Elementary Analysis: | | | | | |
|---|---|---|---|---|---|
| | Ca | P | C | H | Cl |
| Calculated for $C_{24}H_{52}O_8P_2Ca$ (%) | 7.0 | 10.9 | 50.5 | 9.1 | 0.0 |
| Found (%) | 7.0 | 11.0 | 50.3 | 9.0 | 0.0 |

| Infrared Absorption Spectrum (KBr method): | | |
|---|---|---|
| Wave Number ($Cm^{-1}$) | Strength | Attribution |
| 2950 | M | $\nu$ as CH |
| 2920 | S | $\nu$ as $CH_2$ |
| 2850 | M | $\nu$ as $CH_2$ |
| 1470 | W | scissor vibrations of $CH_2$ |
| 1170 | M | $\nu$ C—O |
| 1100 | M | |
| 1075 | S | $\nu$ C—O |
| 940 | M | |
| 930 | M | |
| 840 | W | |

EXAMPLE 2

Ca Salt of Monolauryl Phosphate

Four hundred grams of acetone and 100 g of monolauryl phosphate (molecular weight of 266) were placed in a reactor and mixed for dissolution at 40° C. To the solution was added 150.4 g of an aqueous 10% NaOh solution in 30 minutes followed by mixing at 40 to 50° C. for 1 hour. Subsequently, the reaction solution was cooled down to 30° C., filtered and dried to obtain Na salt of monolauryl phosphate. The white powder was dissolved in 500 g of water at 60° C., followed by gradually dropping an aqueous solution of 27.6 g of $CaCl_2.2H_2O$ in 160 g of water and mixing at 60° C. for 1 hour to complete the reaction. The reaction solution was cooled down to 30° C. and filtered. The resulting filter cake was washed three times with each 500 g of water and once with 400 g of acetone, followed by drying to obtain 93 g of the intended compound in the form of white powder. Observation through a scanning electron microscope revealed that the compound was in the form of needle crystals having a length below 30 μm, but part of the crystals coagulated.

| Elementary Analysis: | | | | | | |
|---|---|---|---|---|---|---|
| | Ca | P | C | H | Na | Cl |
| Calculated for $C_{24}H_{52}O_8P_2Ca$ (%) | 7.0 | 10.9 | 50.5 | 9.1 | 0.0 | 0.0 |
| Found (%) | 6.9 | 10.7 | 50.6 | 9.2 | 0.1 | 0.0 |

EXAMPLE 3

Mg Salt of Monolauryl Phosphate

Four hundred grams of acetone and 100 g of monolauryl phosphate (molecular weight of 266) were placed in a reactor and mixed for dissolution at 40° C. To the solution was added 150.4 g of an aqueous 10% NaOH solution in 30 minutes followed by mixing at 40 to 50° C. for 1 hour. Subsequently, the reaction solution was cooled down to 30° C., filtered and dried to obtain Na salt of monolauryl phosphate. The white powder was dissolved in 500 g of water at 60° C., followed by gradually dropping an aqueous solution of 38.2 g of $MgCl_2.6H_2O$ in 80 g of water and mixing at 60° C. for 1 hour to complete the reaction. The reaction solution was cooled down to 30° C. and filtered. The resulting filter cake was washed three times with each 500 g of water and once with 400 g of acetone, followed by drying to obtain 95 g of the intended compound in the form of white powder. Observation through a scanning electron microscope revealed that the compound was in the form of plate crystals having a length from 5 to 50 μm.

| Elementary Analysis: | | | | | | |
|---|---|---|---|---|---|---|
| | Mg | P | C | H | Na | Cl |
| Calculated for $C_{24}H_{52}O_8P_2Mg$ (%) | 4.4 | 11.2 | 52.0 | 9.4 | 0.0 | 0.0 |
| Found (%) | 4.2 | 11.0 | 51.8 | 9.2 | 0.0 | 0.0 |

EXAMPLE 4

Ba Salt of Monolauryl Phosphate

Four hundred grams of acetone and 100 g of monolauryl phosphate (molecular weight of 266) were placed in a reactor and mixed for dissolution at 40° C. To the solution was added 150.4 of an aqueous 10% NaOH solution in 30 minutes followed by mixing at 40 to 50° C. for 1 hour. Subsequently, the reaction solution was cooled down to 30° C., filtered and dried to obtain Na salt of monolauryl phosphate. The white powder was dissolved in 500 g of water at 60° C., followed by gradually dropping an aqueous solution of 45.9 g of BaCl$_2$.2H$_2$O in 260 g of water and mixing at 60° C. for 1 hour to complete the reaction. The reaction solution was cooled down to 30° C. and filtered. The resulting filter cake was washed three times with each 500 g of water and once with 400 g of acetone, followed by drying to obtain 108 g of the intended compound in the form of white powder. Observation through a scanning electron microscope revealed that the compound was in the form of plate crystals having a length from 5 to 50 μm.

| | Elementary Analysis: | | | | | |
|---|---|---|---|---|---|---|
| | Ba | P | C | H | Na | Cl |
| Calculated for C$_{24}$H$_{52}$O$_8$P$_2$Ba (%) | 20.6 | 9.3 | 43.2 | 7.8 | 0.0 | 0.0 |
| Found (%) | 20.9 | 9.3 | 43.0 | 7.6 | 0.2 | 0.0 |

EXAMPLE 5

Zn salt of Monolauryl Phosphate

Four hundred grams of acetone and 100 g of monolauryl phosphate (molecular weight of 266) were placed in a reactor and mixed for dissolution at 40° C. To the solution was added 150.4 g of an aqueous 10% NaOH solution in 30 minutes followed by mixing at 40 to 50° C. for 1 hour. Subsequently, the reaction solution was cooled down to 30° C., filtered and dried to obtain Na salt of monolauryl phosphate. The white powder was dissolved in 500 g of water at 60° C., followed by gradually dropping an aqueous solution of 54.0 g of ZnSO$_4$.7H$_2$O in 190 g of water and mixing at 60° C. for 1 hour to complete the reaction. The reaction solution was cooled down to 30° C. and filtered. The resulting filter cake was washed three times with each 500 g of water and once with 400 g of acetone, followed by drying to obtain 96 g of the intended compound in the form of white powder. Observation through a scanning electron microscope revealed that the compound was in the form of flaky crystals having a length from 5 to 50 μm.

| | Elementary Analysis: | | | | | |
|---|---|---|---|---|---|---|
| | Zn | P | C | H | Na | Cl |
| Calculated for C$_{24}$H$_{52}$O$_8$P$_2$Zn (%) | 10.9 | 10.4 | 48.4 | 8.7 | 0.0 | 0.0 |
| Found (%) | 11.0 | 10.6 | 48.3 | 8.6 | 0.2 | 0.0 |

EXAMPLE 6

Ca Salt of Monostearyl Phosphate

Four hundred grams of ethanol and 100 g of monostearyl phosphate (molecular weight of 350) were placed in a reactor and mixed for dissolution at 75° C. Into the solution was gradually dropped an aqueous solution of 21.0 g of CaCl$_2$.2H$_2$O in 120 g of water, followed by mixing at 75° C. for 1 hour to complete the reaction. Subsequently, the reaction solution was cooled down to 30° C. and filtered. The resulting filter cake was washed twice with each 400 g of ethanol, once with 500 g of water, and once with 400 g of acetone, followed by drying to obtain 97 g of the intended compound in the form of white powder. Observation through a scanning electron microscope revealed that the compound was in the form of needle crystals having a length below 30 μm.

| | Elementary Analysis: | | | | |
|---|---|---|---|---|---|
| | Ca | P | C | H | Cl |
| Calculated for C$_{36}$H$_{76}$O$_8$P$_2$Ca (%) | 5.4 | 8.4 | 58.5 | 10.3 | 0.0 |
| Found (%) | 5.3 | 8.6 | 58.3 | 10.2 | 0.0 |

EXAMPLE 7

Ca Salt of Monostearyl Phosphate

Four hundred grams of ethanol and 100 g of monostearyl phosphate (molecular weight of 350) were placed in a reactor and mixed for dissolution at 75° C. To the solution was added 114.3 g of an aqueous 10% NaOh solution in 30 minutes followed by mixing at 60° to 70° C. for 1 hour. Subsequently, the reaction solution was cooled down to 30° C., filtered and dried to obtain Na salt of monostearyl phosphate. The white powder was mixed with in 500 g of water and dissolved at 70° C., followed by gradually dropping an aqueous solution of 21.0 g of CaCl$_2$.2H$_2$O in 120 g of water and mixing at 70° C. for 1 hour to complete the reaction. The reaction solution was cooled down to 30° C. and filtered. The resulting filter cake was washed three times with each 500 g of water and once with 400 g of acetone, followed by drying to obtain 94 g of the intended compound in the form of white powder. Observation through a scanning electron microscope revealed that the compound was in the form of needle crystals having a length below 30 μm.

| | Elementary Analysis: | | | | | |
|---|---|---|---|---|---|---|
| | Ca | P | C | H | Na | Cl |
| Calculated for C$_{36}$H$_{76}$O$_8$P$_2$Ca (%) | 5.4 | 8.4 | 58.5 | 10.3 | 0.0 | 0.0 |
| Found (%) | 5.2 | 8.4 | 58.6 | 10.4 | 0.1 | 0.0 |

COMPARATIVE EXAMPLE 1

Ca Salt of Monolauryl Phosphate

Four hundred grams of acetone and 100 g of monolauryl phosphate (molecular weight of 266) were placed in a reactor and mixed for dissolution at 40° C. To the solution was added 188 g of an aqueous 10% NaOh solution in 30 minutes, followed by mixing at 40 to 50° C. for 1 hour. The resulting reaction solution was cooled down to 30° C., filtered and dried to obtain a white powder. The powder was dissolved in 500 g of water at 60° C., into which was gradually dropped an aqueous solution of 27.6 g of CaCl$_2$.2H$_2$O in 160 g of water, followed by mixing at 60° C. for 1 hour to complete the reaction. Subsequently, the reaction solution was cooled down to 30° C. and filtered. The resulting filter cake was washed three times with each 500 g of water and once with 400 g of acetone, followed by drying to obtain a compound in the form of white powder. Observation through a scanning electron microscope revealed that no specific crystal form was recognized.

| Elementary Analysis: | | | | | |
| --- | --- | --- | --- | --- | --- |
| | Ca | P | C | H | Na | Cl |
| Found (%) | 6.8 | 10.5 | 49.6 | 8.7 | 2.0 | 0.0 |

COMPARATIVE EXAMPLE 2

Ca Salt of Monolauryl Phosphate

Four hundred grams of acetone and 100 g of monolauryl phosphate (molecular weight of 266) were placed in a reactor and mixed for dissolution at 40° C. To the solution was added 300.8 g of an aqueous 10% NaOH solution in 30 minutes, followed by mixing at 40 to 50° C. for 1 hour. The resulting reaction solution was cooled down to 30° C., filtered and dried to obtain a disodium salt of monolauryl phosphate. The white powder was dissolved in 500 g of water at 60° C., into which was gradually dropped an aqueous solution of 27.6 g of $CaCl_2 \cdot 2H_2O$ in 160 g of water, followed by mixing at 60° C. for 1 hour to complete the reaction. Subsequently, the reaction solution was cooled down to 30° C. and filtered. The resulting filter cake was washed three times with each 500 g of water and once with 400 g of acetone, followed by drying to obtain a compound in the form of white powder. Observation through a scanning electron microscope revealed that no specific crystal form was recognized.

| Elementary Analysis: | | | | | |
| --- | --- | --- | --- | --- | --- |
| | Ca | P | C | H | Na | Cl |
| Found (%) | 8.2 | 9.5 | 44.9 | 7.9 | 4.4 | 0.0 |

COMPARATIVE EXAMPLE 3

Ca Salt of Monolauryl Phosphate

Four hundred grams of acetone and 100 g of monolauryl phosphate (molecular weight of 266) were placed in a reactor and mixed for dissolution at 40° C. To the solution was added 300.8 g of an aqueous 10% NaOH solution in 30 minutes, followed by mixing at 40 to 50° C. for 1 hour. The resulting reaction solution was cooled down to 30° C., filtered and dried to obtain a disodium salt of monolauryl phosphate. The white powder was dissolved in 500 g of water at 60° C., into which was gradually dropped an aqueous solution of 55.2 g of $CaCl_2 \cdot 2H_2O$ in 320 g of water, followed by mixing at 60° C. for 1 hour to complete the metal conversion reaction. Subsequently, the reaction solution was cooled down to 30° C. and filtered. The resulting filter cake was washed three times with each 500 g of water and once with 400 g of acetone, followed by drying to obtain a compound in the form of white powder. Observation through a scanning electron microscope revealed that no specific crystal form was recognized.

| Elementary Analysis: | | | | | |
| --- | --- | --- | --- | --- | --- |
| | Ca | P | C | H | Na | Cl |
| Found (%) | 12.7 | 9.9 | 46.3 | 8.4 | 0.4 | 0.0 |

The starting materials, reaction conditions and crystal forms of final products in Examples 1 through 7 and Comparative Examples 1 through 3 are summarized in Tables 1 and 2.

TABLE 1

| Example | | 1 | 2 | 3 | 4 | 5 | 6 | 7 |
| --- | --- | --- | --- | --- | --- | --- | --- | --- |
| Starting Metal | M | Ca | Ca | Mg | Ba | Zn | Ca | Ca |
| Salt | X | Cl | Cl | Cl | Cl | $SO_4$ | Cl | Cl |
| Starting Monoalkyl Phosphate** | | Lauryl | Lauryl | Lauryl | Lauryl | Lauryl | Stearyl | Stearyl |
| Reactions Conditions | | | | | | | | |
| Neutrality of Monoalkyl Phosphate* | | 0 | 1.0 | 1.0 | 1.0 | 1.0 | 0 | 1.0 |
| Metal Ions/Monoalkyl Phosphate (Molar Ratio) | | 0.5 | 0.5 | 0.5 | 0.5 | 0.5 | 0.5 | 0.5 |
| Crystal Form of Product | | Needle | Plate | Plate | Plate | Flake | Needle | Needle |

**Purity over 99%

TABLE 2

| Comparative Example | | 1 | 2 | 3 |
| --- | --- | --- | --- | --- |
| Starting Metal Salt | M | Ca | Ca | Ca |
| | X | Cl | Cl | Cl |
| Starting Composition (%) | | | | |
| Monolauryl Phosphate | | over 99 | over 99 | over 99 |
| Dilauryl Phosphate | | — | — | — |
| Phosphoric Acid | | — | — | — |
| Reactions Conditions | | | | |
| Neutrality of Lauryl Phosphate* | | 1.25 | 2.0 | 2.0 |
| Metal Ions/Lauryl Phosphate (Molar ratio) | | 0.5 | 0.5 | 1.0 |
| Crystal Form of Product | | Amorphous | Amorphous | Amorphous |

*Neutralization of phosphoric ester in the 1st equivalence point is defined as neutrality 1.0

EXAMPLE 8

Ca Salt of Monolauryl Phosphate 15.4 g (0.38 moles) of NaOH, 540 g of water and 60 g of ethanol were placed in a reactor and mixed at 30° C. To the mixture was added 100 g (0.376 moles) of monolauryl phosphate (molecular weight of 266), followed by mixing at 50° C. Subsequently, an aqueous solution of 27.5 g (0.188 moles) of $CaCl_2 \cdot 2H_2O$ in 100 g of water was gradually dropped into the mixture, followed by mixing at 60° C. for 1 hour to complete the reaction. The reaction solution was cooled down to 30° C. and filtered. The resulting cake was washed three times with each 500 g of water and once with 400 g of acetone and dried to obtain 97 g of the intended compound in the form of white powder. Observation through a scanning electron microscope revealed that a compound was in the form of needle crystals having a length below 30 μm without involving coagulation of the crystals.

EXAMPLE 9

Figure 1:
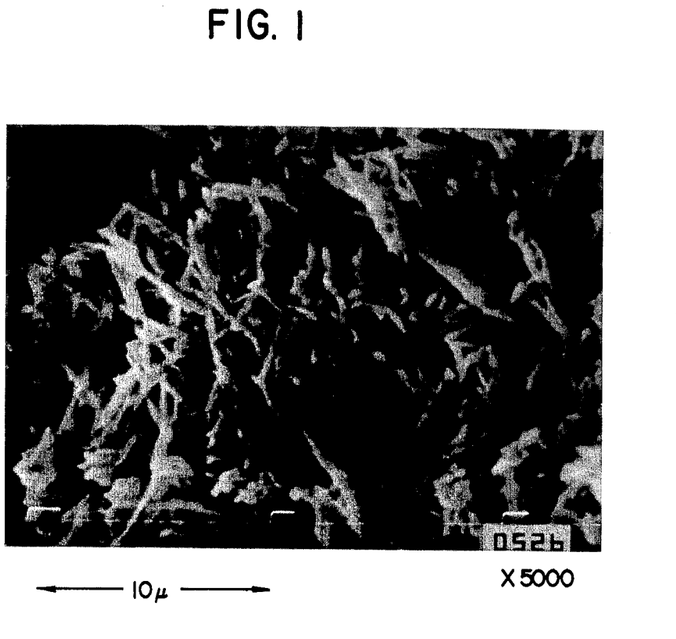
FIG. 1 is an electron microphotograph showing the crystal structure of calcium salt of monolauryl phosphate obtained in Example 9.

Ca Salt of Monolauryl Phosphate 15.4 g (0.38 moles) of NaOH, 200 g of water and 50 g of ethanol were placed in a reactor and mixed at 30° C. To the mixture was added 100 g (0.376 moles) of monolauryl phosphate (molecular weight of 266), followed by mixing at 50° C. Subsequently, an aqueous solution of 27.5 g (0.188 moles) of $CaCl_2.2H_2O$ in 100 g of water was gradually dropped into the mixture, followed by mixing at 60° C. for 1 hour to complete the reaction. The reaction solution was cooled down to 30° C. and filtered. The resulting cake was washed three times with each 500 g of water and once with 400 g of acetone and dried to obtain 99 g of the intended compound in the form of white powder. Observation through a scanning electron microscope revealed that the compound was in the form of needle crystals having a length below 30 μm. The electron microphotograph of the crystals is shown in FIG. 1.

EXAMPLE 10

Ca Salt of Monolauryl Phosphate 15.4 g (0.38 moles) of NaOH, 50 g of water and 50 g of ethanol were placed in a reactor and mixed at 30° C. To the mixture was added 100 g (0.376 moles) of monolauryl phosphate (molecular weight of 266), followed by mixing at 50° C. Subsequently, an aqueous solution of 27.5 g (0.188 moles) of $CaCl_2.2H_2O$ in 100 g of water was gradually dropped into the mixture, followed by mixing at 60° C. for 1 hour to complete the reaction. The reaction solution was cooled down to 30° C. and filtered. The resulting cake was washed three times with each 500 g of water and once with 400 g of acetone and dried to obtain 98 g of the intended compound in the form of white powder. Observation through a scanning electron microscope revealed that the compound was in the form of needle crystals having a length below 30 μm.

EXAMPLE 11

Zn Salt of Monolauryl Phosphate 15.4 g (0.38 moles) of NaOH, 200 g of water and 50 g of acetone were placed in a reactor and mixed at 30° C. The the mixture was added 100 g (0.376 moles) of monolauryl phosphate (molecular weight of 266), followed by mixing at 50° C. Subsequently, an aqueous solution of 54 g (0.188 moles) of $ZnSO_4.7H_2O$ in 100 g of water was gradually dropped into the mixture, followed by mixing at 60° C. for 1 hour to complete the reaction. The reaction solution was cooled down to 30° C. and filtered. The resulting cake was washed three times with each 500 g of water and once with 400 g of acetone and dried to obtain 95 g of the intended compound in the form of white powder. Observation through a scanning electron microscope revealed that the compound was in the form of flaky crystals having a length of 5 to 50 μm.

EXAMPLE 12

Ba Salt of Monolauryl Phosphate 15.4 g (0.38 moles) of NaOH, 200 g of water and 50 g of acetone were placed in a reactor and mixed at 30° C. To the mixture was added 100 g (0.376 moles) of monolauryl phosphate (molecular weight of 266), followed by mixing at 50° C. Subsequently, an aqueous solution of 45.9 (0.188 moles) of $BaCl_2.2H_2O$ in 100 g of water was gradually dropped into the mixture, followed by mixing at 60° C. for 1 hour to complete the reaction. The reaction solution was cooled down to 30° C. and filtered. The resulting cake was washed three times with each 500 g of water and once with 400 g of acetone and dried to obtain 103 g of the intended compound in the form of white powder. Observation through a scanning electron microscope revealed that the compound was in the form of plate crystals having a length of 5 to 50 μm.

EXAMPLE 13

Ca Salt of Monostearyl Phosphate 11.5 g (0.288 moles) of NaOH, 200 g of water, and 50 g of acetone were placed in a reactor and mixed at 30° C. To the mixture was added 100 g (0.286 moles) of monostearyl phosphate (molecular weight of 350), followed by mixing at 60° to 70° C. Subsequently, an aqueous solution of 20.9 g (0.143 moles) of $CaCl_2.2H_2O$ in 75 g of water was gradually dropped into the mixture, followed by mixing at 70° C. for 1 hour to complete the reaction. The reaction solution was cooled down to 30° C. and filtered. The resulting cake was washed three times with each 500 g of water and once with 400 g of acetone and dried to obtain 96 g of the intended compound in the form of white powder. Observation through a scanning electron microscope revealed that the compound was in the form of needle crystals having a length below 30 μm.

EXAMPLE 14

Zn Salt of Monostearyl Phosphate 11.5 g (0.288 moles) of NaOH, 200 g of water and 50 g of ethanol were placed in a reactor and mixed at 30° C. To the mixture was added 100 g (0.286 moles) of monostearyl phosphate (molecular weight of 350), followed by mixing at 60° to 70° C. Subsequently, an aqueous solution of 41 g (0.143 moles) of $ZnSO_4.7H_2O$ in 75 g of water was gradually dropped into the mixture, followed by mixing at 70° C. for 1 hour to complete the reaction. The reaction solution was cooled down to 30° C. and filtered. The resulting cake was washed three times with each 500 g of water and once with 400 g of acetone and dried to obtain 96 g of the intended compound in the form of white powder. Observation through a scanning electron microscope revealed that the compound was in the form of flaky crystals having a length of from 5 to 50 μm.

EXAMPLE 15

Ca Salt of Monolauryl Phosphate 15.4 g (0.38 moles) of NaOH and 250 g of water were placed in a reactor and mixed at 30° C. To the mixture was added 100 g (0.376 moles) of monolauryl phosphate (molecular weight of 266), followed by mixing at 50° C. Subsequently, an aqueous solution of 27.5 g (0.188 moles) of $CaCl_2.2H_2O$ in 100 g of water was gradually dropped into the mixture, followed by mixing at 60° C. for 1 hour to complete the reaction. The reaction solution was cooled down to 30° C. and filtered. The resulting cake was washed three times with each 500 g of water and once with 400 g of acetone and dried to obtain 97 g of the intended compound in the form of white powder. Observation through a scanning electron microscope revealed that the crystals coagulated and no needle crystals were recognized.

EXAMPLE 16

The powders obtained in Examples 1 through 15 and Comparative Examples 1 through 3 were organoleptically examined by 10 expert panels with regard to the feel of the powders themselves. Moreover, the respective powders were subjected to measurement of abrasion resistance using a surface tester, Heidon 14, made by Shinto Scientific Co., Ltd. The results are shown in Table 3.

| Formulation: | |
|---|---|
| (6) Yellow iron oxide | 0.1 |
| (7) Black iron oxide | 0.01 |
| (8) Perfume | 0.5 |
| Total | 100.0 |

Preparation:

(1) through (7) were mixed in a Henschel mixer, to which (8) was added and mixed, followed by press molding.

TABLE 3

| Compound | | Synthetic Method | Organoleptic Evaluation* | | | | Friction Coefficient |
|---|---|---|---|---|---|---|---|
| | | | Spreadability | Softness | Adherence | Covering Power | |
| Ca Salt of Monolauryl Phosphate | | Example 1 | +2 | +1.5 | +0.8 | +0.7 | $0.4 \times 10^{-2}$ |
| | | Example 2 | +2 | +1.5 | +0.7 | +0.7 | $0.4 \times 10^{-2}$ |
| | | Example 8 | +2 | +1.5 | +0.8 | +0.7 | $0.4 \times 10^{-2}$ |
| | | Example 9 | +2 | +1.5 | +0.8 | +0.7 | $0.4 \times 10^{-2}$ |
| | | Example 10 | +2 | +1.5 | +0.7 | +0.7 | $0.4 \times 10^{-2}$ |
| | | Comparative Example 1 | +1.3 | +1.5 | +0.8 | +0.7 | $0.55 \times 10^{-2}$ |
| | | Comparative Example 2 | +1.2 | +1.5 | +0.7 | +0.6 | $0.6 \times 10^{-2}$ |
| | | Comparative Example 3 | +1.2 | +1.5 | +1.0 | +0.8 | $0.6 \times 10^{-2}$ |
| | | Example 15 | +1.7 | +1.5 | +0.8 | +0.7 | $0.45 \times 10^{-2}$ |
| Monolauryl Phosphate | Mg salt | Example 3 | +2 | +1.7 | +0.5 | +0.5 | $0.45 \times 10^{-2}$ |
| | Ba salt | Example 4 | +2 | +1.5 | +0.5 | +0.5 | $0.45 \times 10^{-2}$ |
| | Zn salt | Example 5 | +2 | +1.5 | +0.5 | +0.5 | $0.45 \times 10^{-2}$ |
| Ca Salt of Monostearyl Phosphate | | Example 6 | +2 | +1.4 | +0.5 | +0.7 | $0.4 \times 10^{-2}$ |
| | | Example 7 | +2 | +1.3 | +0.5 | +0.6 | $0.4 \times 10^{-2}$ |
| Zn Salt of Monostearyl Phosphate | | Example 2** | +2 | +1.3 | +1 | +0.5 | $0.4 \times 10^{-2}$ |
| | | Example 14 | +2 | +1.4 | +0.5 | +0.7 | $0.45 \times 10^{-2}$ |
| Monocetyl Phosphate | Ca salt | Example 2** | +2 | +2 | +0.7 | +0.3 | $0.3 \times 10^{-2}$ |
| | Mg salt | Example 2** | +2 | +1.5 | +0.7 | +0.4 | $0.35 \times 10^{-2}$ |
| | Zn salt | Example 2** | +2 | +1.5 | +0.5 | +0.2 | $0.35 \times 10^{-2}$ |
| Mg Salt of Monostearyl Phosphate | | Example 2** | +2 | +1.2 | +1 | +0.6 | $0.4 \times 10^{-2}$ |
| Palmitic Acid | Ca salt | — | −1 | +0.1 | +0.5 | +1.5 | $1.3 \times 10^{-2}$ |
| | Mg salt | — | −1.2 | −0.1 | +0.7 | +1.2 | $1.4 \times 10^{-2}$ |
| | Zn salt | — | −1.5 | 0 | +1 | +1.3 | $1.4 \times 10^{-2}$ |
| Stearic Acid | Ca salt | — | −1.2 | −0.3 | +0.5 | +1.5 | $1.\% \times 10^{-2}$ |
| | Mg salt | — | −1 | +0.1 | +0.7 | +1.5 | $1.4 \times 10^{-2}$ |
| | Zn salt | — | −1.5 | 0 | +0.5 | +1.2 | $1.5 \times 10^{-2}$ |
| Nylon Powder | | — | +1.5 | −2 | −2 | −2 | $0.55 \times 10^{-2}$ |

Example 2**: prepared in the same manner as in Example 2.
Organoleptic evaluation standards*: the respective items were evaluated according to the following standards. The figures in the table indicate average values of evaluation of ten panelers.
Very good: +2,
Good: +1,
Moderate: 0,
Poor: −1,
Very poor: −2

The above results demonstrate that the products of the present invention have good spreadability, softness, smoothness, suitable degrees of adherence and transparency, and covering power.

Example 17

The powder of the present invention and the powder for comparison were used as a feel modifier to make pressed face powders of the following formulation. The face powders were organoleptically evaluated by 10 expert panelers according to a paired comparison. The results are shown in Tables 4 through 6.

| Formulation: | |
|---|---|
| (1) Feel modifier (Table 4) | 5.0% |
| (2) Talc | 87.74 |
| (3) Liquid paraffin | 5.0 |
| (4) Titanium dioxide | 1.5 |
| (5) Red iron oxide | 0.15 |

TABLE 4

| Feel Modifier | Number of Panelers Favoring Cosmetic Properties | | | | |
|---|---|---|---|---|---|
| | Spreadability | Smoothness | Softness | Adherence | Covering Power |
| Powder obtained in Example 1 | 8 | 8 | 6 | 5 | 6 |
| Powder obtained in Com. Ex. 1 | 2 | 2 | 4 | 5 | 4 |

TABLE 5

| Feel Modifier | Number of Panelers Favoring Cosmetic Properties | | | | |
|---|---|---|---|---|---|
| | Spreadability | Smoothness | Softness | Adherence | Covering Power |
| Calcium salt of monocetyl | 10 | 10 | 10 | 8 | 8 |

TABLE 5-continued

| Feel Modifier | Number of Panelers Favoring Cosmetic Properties | | | | |
|---|---|---|---|---|---|
| | Spread-ability | Smooth-ness | Soft-ness | Adher-ence | Cover-ing Power |
| phosphate obtained in the same manner as in Ex. 2 | | | | | |
| Calcium palmitate for comparison | 0 | 0 | 0 | 2 | 2 |

TABLE 6

| Feel Modifier | Number of Panelers Favoring Cosmetic Properties | | | | |
|---|---|---|---|---|---|
| | Spread-ability | Smooth-ness | Soft-ness | Adher-ence | Cover-ing Power |
| Powder obtained in Example 9 | 7 | 7 | 6 | 5 | 5 |
| Powder obtained in Example 15 | 3 | 3 | 4 | 5 | 5 |

EXAMPLE 18

Figure 2:
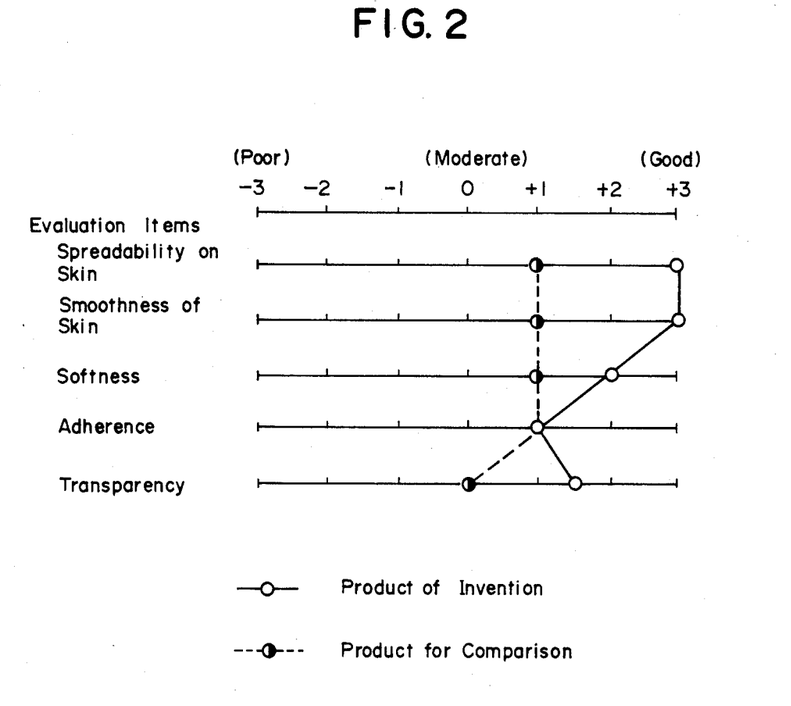
FIGS. 2 through 4 are views showing organoleptic evaluation results of powder foundations of Examples 18 through 20, respectively.

The Ca salt of monolauryl phosphate obtained in Example 1 and the Ca salt of monolauryl phosphate obtained in Comparative Example 3 were provided as the feel modifier and used to prepare powder foundations of the following formulation. The resulting foundations were subjected to organoleptic examination by ten expert panelers. The results are shown in FIG. 2.

| Formulation: | |
|---|---|
| (1) Feel modifier | 5.0% |
| (2) Sericite | 79.5 |
| (3) Liquid paraffin | 5.0 |
| (4) Lanolin | 2.0 |
| (5) Isopropyl myristate | 1.0 |
| (6) Titanium dioxide | 5.0 |
| (7) Red iron oxide | 1.0 |
| (8) Yellow iron oxide | 1.0 |
| (9) Black iron oxide | 0.2 |
| (10) Perfume | 0.3 |
| Total | 100.0 |

Preparation:
(1) through (9) were mixed in a Henschel mixer, to which (10) was added and mixed, followed by press molding.

Results:
As shown in FIG. 2, the foundation product of the invention is better than the product for comparison with respect top spreadability, smoothness and has good softness and suitable degrees of transparency and covering power.

EXAMPLE 19

Figure 3:
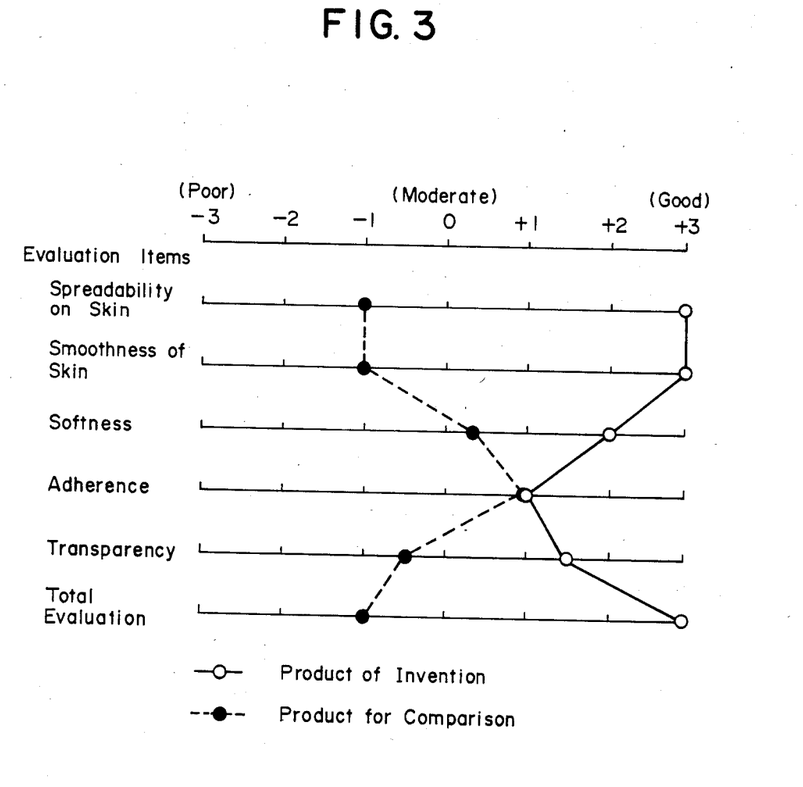

The calcium salt of monostearyl phosphate prepared in the same manner as in Example 2 and a comparative compound of calcium palmitate were provided as a feel modifier, followed by preparing powder foundations in the same manner as in Example 18. The foundations were organoleptically evaluated with the results shown in FIG. 3. From the figure, it will be seen that the product of the invention is better than the comparative product with respect to spreadability and smoothness and has good softness and suitable degrees of transparency and covering power.

EXAMPLE 20

Figure 4:
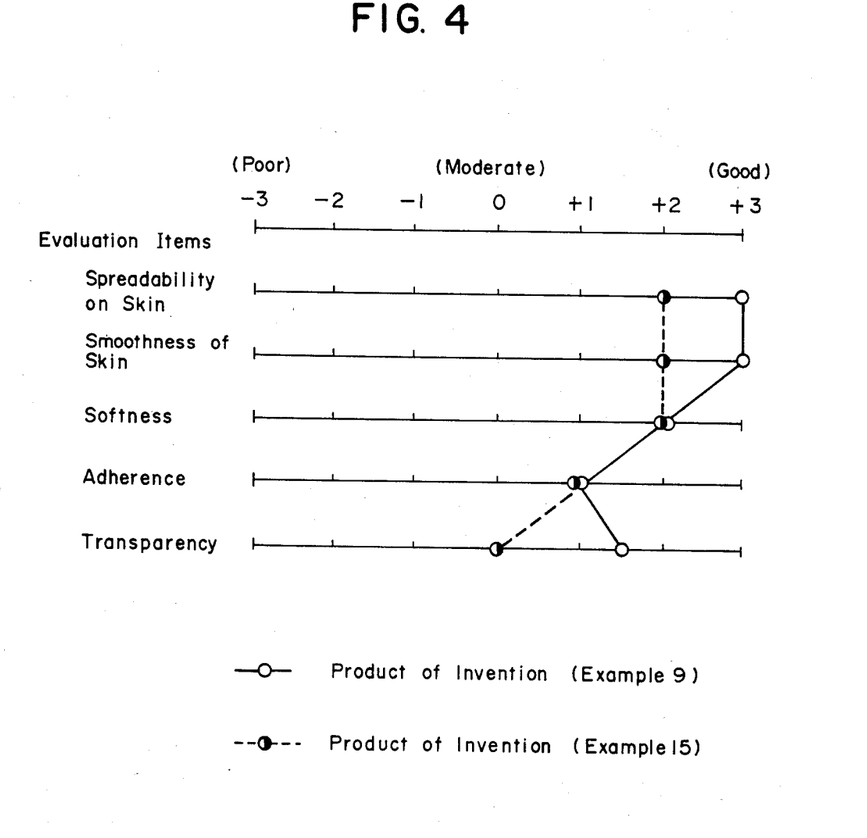

The general procedure of Example 18 was repeated using, as the feel modifier, the calcium salt of monolauryl phosphate obtained in Example 9 and the calcium salt of monolauryl phosphate obtained in Example 15, thereby obtaining powder foundations. These foundations were organoleptically evaluated. The results are shown in FIG. 4.

EXAMPLE 21

Eye Shadow:

| Formulation: | |
|---|---|
| (1) Titanium dioxide-coated mica | 90.7% |
| (2) Zn salt of monolauryl phosphate | 5.0 |
| (3) Squalane | 4.0 |
| (4) Perfume | 0.3 |
| Total | 100.0 |

Preparation:
(1) through (3) were mixed in a Henschel mixer, to which (4) was added and mixed, followed by press molding. As a result, there was obtained an eye shadow which had very good smoothness and spreadability along with good softness and adherence.

What is claimed is:

1. A cosmetic composition comprising cosmetic powder and a metal salt of a monoalkyl phosphate of the general formula (I)

$$RO-\overset{O}{\underset{OH}{\overset{\|}{P}}}-O-M-O-\overset{O}{\underset{OH}{\overset{\|}{P}}}-OR \quad (I)$$

in which each R represents a saturated or unsaturated, linear or branched hydrocarbon group having from 8 to 32 carbon atoms, and M represents an alkaline earth metal or divalent transition metal, said compositions having a suitable degree of spreadability, moistness, smoothness, adherence and covering properties.

2. The cosmetic composition of claim 1, wherein M is selected from the group consisting of Mg, Ca and Ba.

3. The cosmetic composition of claim 1, wherein M is selected from the group consisting of Zn, Cu, Ni, Co, Fe, Mn, Cd, Pb, Cr and Ti.

4. The cosmetic composition of claim 3, wherein M is selected from the group consisting of Zn, Fe and Ni.

5. The cosmetic composition of claim 1, wherein R is selected from the group consisting of octyl, nonyl, decyl, dodecyl, undecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, octenyl, nonenyl, decenyl, dodecenyl, undecenyl, tridecenyl, tetradecenyl, pentadecenyl, hexadecenyl, heptadecenyl, octadecenyl, nonadecenyl, eicocenyl, heneicocenyl, dococenyl, tricocenyl, tetracocenyl, pentacocenyl, hexacocenyl, heptacocenyl, octacocenyl, nonacocenyl, triaconetenyl, hentriacontenyl, dotriacontenyl, octadienyl, nonadienyl, decadienyl, dodecadienyl, undecadienyl, tridecadienyl, tetradecadienyl, pentadecadienyl, hexadecadienyl, heptadecadienyl, octadecadienyl, nonadecadienyl, eicosadienyl, heneicosadienyl, docosadienyl, tricosadienyl, tetracosadienyl, pentacosadienyl, hexacosadienyl, heptacosadienyl, octacosadienyl, nonacosadienyl, triacontadienyl, hentriacontadienyl, dotriacontadienyl, 2-hexyldecyl, 2-octylundecyl, 2-decyltetradecyl, 2-undecylhexadecyl and 2-tetradecyloctadecyl groups.

6. The cosmetic composition of claim 5, wherein R is a dodecyl or octadecyl group.

7. The composition of claim 1, further comprising at least one member selected from the group consisting of oils, surface active agents, humectants, preservatives, antioxidants and perfumes.

* * * * *